United States Patent
Monllor et al.

(10) Patent No.: US 10,385,488 B1
(45) Date of Patent: Aug. 20, 2019

(54) SUTURE OF VARYING CROSS-SECTION AND METHODS OF MANUFACTURE AND USE

(71) Applicant: Stryker Corporation, Kalamazoo, MI (US)

(72) Inventors: Carlos Benitez Monllor, Ponce, PR (US); Ross Callison, Denver, CO (US); José Raúl Marchand, San Juan, PR (US); Logan Renwick, Denver, CO (US)

(73) Assignee: Stryker Corporation, Kalamazoo, MI (US)

( * ) Notice: Subject to any disclaimer, the term of this patent is extended or adjusted under 35 U.S.C. 154(b) by 807 days.

(21) Appl. No.: 15/014,580

(22) Filed: Feb. 3, 2016

Related U.S. Application Data

(60) Provisional application No. 62/111,367, filed on Feb. 3, 2015.

(51) Int. Cl.
*D04C 1/12* (2006.01)
*A61B 17/06* (2006.01)

(52) U.S. Cl.
CPC .......... *D04C 1/12* (2013.01); *A61B 17/06166* (2013.01); *A61B 2017/0619* (2013.01)

(58) Field of Classification Search
CPC ........................ A61B 17/06166; D04C 1/12
See application file for complete search history.

(56) References Cited

U.S. PATENT DOCUMENTS

| | | | | |
|---|---|---|---|---|
| 2,441,601 A | * | 5/1948 | Selby | A61B 17/04 57/31 |
| 3,730,821 A | * | 5/1973 | Jackson | B29D 28/00 428/105 |
| 3,926,194 A | * | 12/1975 | Greenberg | A61B 17/06004 163/5 |
| 3,949,755 A | | 4/1976 | Vauquois | |
| 4,034,763 A | | 7/1977 | Frazier | |
| 4,510,934 A | | 4/1985 | Batra | |
| 4,792,336 A | | 12/1988 | Hlavacek et al. | |
| 4,806,737 A | | 2/1989 | Coates | |
| 4,832,025 A | | 5/1989 | Coates | |
| 5,007,922 A | | 4/1991 | Chen et al. | |

(Continued)

OTHER PUBLICATIONS

U.S. Appl. No. 62/177,533, filed Mar. 16, 2015.
U.S. Appl. No. 14/553,474, filed Nov. 25, 2014.

*Primary Examiner* — Shaun R Hurley
(74) *Attorney, Agent, or Firm* — Lerner, David, Littenberg, Krumholz & Mentlik, LLP

(57) ABSTRACT

The present invention includes, in one embodiment, a method of forming a suture having various cross-sectional shapes, the method including the steps of braiding the suture such that the suture has a first cross-sectional shape along a length; holding a first end of the suture and holding the suture at a second position at a location in between the first end and a second end such that a first portion of the suture is defined between the first end and the second position; manipulating the first end relative to the second position to alter the first portion of the suture into an altered cross-sectional shape different from the first cross-sectional shape; and releasing the first end and the second position, wherein the step of manipulating is performed such that, upon release, the first portion maintains its manipulated shape.

20 Claims, 4 Drawing Sheets

(56) References Cited

U.S. PATENT DOCUMENTS

| | | | |
|---|---|---|---|
| 5,226,336 | A | 7/1993 | Coates |
| 5,250,247 | A | 10/1993 | Chesterfield et al. |
| 5,314,446 | A | 5/1994 | Hunter et al. |
| 5,318,575 | A | 6/1994 | Chesterfield et al. |
| 5,452,636 | A | 9/1995 | Rattan |
| 5,454,834 | A | 10/1995 | Boebel et al. |
| 5,456,722 | A | 10/1995 | McLeod et al. |
| 5,478,216 | A | 12/1995 | Neward |
| 5,540,703 | A | 7/1996 | Barker, Jr. et al. |
| 5,645,568 | A | 7/1997 | Chervitz et al. |
| 5,726,422 | A | 3/1998 | Haase et al. |
| 5,792,181 | A | 8/1998 | Haase et al. |
| 5,813,303 | A | 9/1998 | Haase et al. |
| 5,829,979 | A | 11/1998 | Kobashigawa et al. |
| 5,855,156 | A | 1/1999 | Haase et al. |
| 5,891,166 | A | 4/1999 | Schervinsky |
| 5,975,876 | A | 11/1999 | Haase et al. |
| 6,001,121 | A | 12/1999 | Haase et al. |
| 6,035,751 | A | 3/2000 | Haase et al. |
| 6,045,571 | A | 4/2000 | Hill et al. |
| 6,053,086 | A | 4/2000 | Smyth |
| 6,309,202 | B1 | 10/2001 | Demarest et al. |
| 6,319,445 | B1 | 11/2001 | Haase et al. |
| 6,716,234 | B2 | 4/2004 | Grafton |
| 6,994,719 | B2 | 2/2006 | Grafton |
| 7,029,490 | B2 | 4/2006 | Grafton et al. |
| 7,892,256 | B2 | 2/2011 | Grafton et al. |
| 8,012,172 | B2 | 9/2011 | Grafton et al. |
| 8,088,146 | B2 | 1/2012 | Wert et al. |
| 8,222,564 | B2 | 7/2012 | Maiorino et al. |
| 8,672,966 | B2 | 3/2014 | Wert et al. |
| 2005/0119696 | A1 | 6/2005 | Walters et al. |
| 2013/0131722 | A1 | 5/2013 | Marchand et al. |

\* cited by examiner

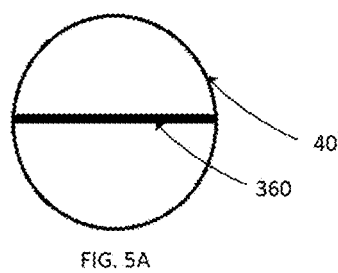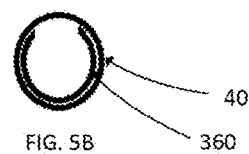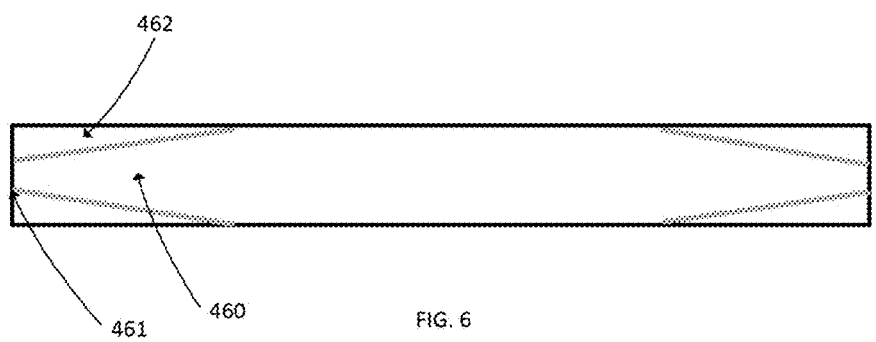

SUTURE OF VARYING CROSS-SECTION AND METHODS OF MANUFACTURE AND USE

CROSS-REFERENCE TO RELATED APPLICATION

This application claims the benefit of the filing date of U.S. Provisional Patent Application No. 62/111,367 filed on Feb. 3, 2015, the disclosure of which is hereby incorporated herein by reference.

BACKGROUND

Sutures are available in a variety of materials, shapes and sizes. One such shape is a "flat" suture, where a plurality of fibers are braided such that the resulting suture is significantly wider than it is tall, resulting in a flat, or planar shape. Such sutures can be useful, for example, in increasing the contact surface area between the suture and the underlying soft tissue to help increase the contact footprint of the soft tissue against the underlying bone. This is particularly useful in, for example, rotator cuff repairs where a "suture bridge" is formed over the upper surface of the cuff to compress the cuff tissue to the underlying bone. Another advantage of such flat sutures is that the larger surface area distributes forces exerted on the tissue by the suture such that there is less of a chance the suture will cut into the tissue relative to a thinner suture (e.g., a traditional round suture).

Current flat sutures on the market, however, suffer from multiple drawbacks such that surgeons have been slow to utilize them. For example, the shape of the flat suture often times requires different instrumentation, thereby rendering much of the instrumentation on the market incompatible with such flat sutures. Commonly, surgeons have been using a particular instrument for a long time and are unwilling to change just to accommodate a differently-shaped suture. Another drawback of current flat sutures occurs when a surgeon attempts to tie the flat suture in a knot. Typically, the flat shape of the braided suture does not compress well, and thus the resulting knot easily loosens, or worse, comes completely undone.

Thus, there is a need in the art for a flat suture that is compatible with instrumentation on the market and which can be manipulated and handled effectively by traditional methods, such as when forming a secure knot.

SUMMARY OF THE INVENTION

In one embodiment, the present invention is a method of forming a suture having various cross-sectional shapes, the method including obtaining a length of suture having a first cross-section, manipulating a portion of the suture, and releasing the portion of the suture such that at least part of the portion maintains its manipulated shape. In this embodiment, the manipulation results in the portion of the suture having a different cross-section shape than the first cross-section. For example, the first cross-section may be generally flat or rectangular, while the portion undergoes a twisting manipulation such that the portion obtains a rounded shape (e.g., round, circular, ovular, or the like). The manipulated portion may include a first end of the length of suture and extend partway along the length of the suture. Further, a second portion may be similarly manipulated as the first portion. For example, the second portion may include a second end of the length of suture and extend partway along the length of the suture. Preferably, the first and second portions are separated by a third portion that maintains the first cross-section and does not undergo the manipulation step. Preferably, both the first and second portions undergo a twisting manipulation.

In another embodiment, the present invention is a method of forming a suture having various cross-sectional shapes, the method including the steps of forming the suture such that the suture has a first cross-section along a length; holding a first end of the suture and holding the suture at a second position at a location in between the first end and a second end such that a first portion of the suture is defined between the first end and the second location; manipulating the first portion to form a manipulated shape; and releasing the first end and the second position, wherein the step of manipulating is performed such that, upon release, the first portion maintains its manipulated shape.

For example, the manipulating step includes twisting such that the manipulating and releasing steps of the above method include twisting the first end relative to the second position to twist the first portion of the suture around itself to form a twisted shape; and releasing the first end and the second position, wherein the step of twisting is performed with a number of twists and at a specific tension such that, upon release, the first portion remains twisted.

The forming step may be performed by, for example, braiding a plurality of fibers together to form the suture. The method may further include the step of, after twisting, applying a stiffening agent to the first portion to reinforce the first portion in the twisted configuration. The stiffening agent may be energy applied to at least part of the first portion, and may also include a mechanical force applied to at least part of the first portion. For example, the energy may be heat, and further, the mechanical force may be a heating plate. Alternatively, the stiffening agent may include a coating, glue, or outer tubing positioned on at least part of the first portion.

Continuing with this embodiment, the first cross-section may be generally rectangular or flat. Further, the cross-section of the first portion following manipulation may be generally rounded.

This embodiment may further include the steps of holding a second end of the suture and holding the suture at a fourth position at a location in between the second position and the second end such that a second portion of the suture is defined between the second end and the fourth location; manipulating the second portion of the suture to form a manipulated shape; and releasing the second end and the fourth position, wherein the step of manipulating is performed such that, upon release, the second portion maintains its manipulated shape.

As mentioned above relative to the first portion, these additional manipulating and releasing steps of the second portion can include twisting the second end relative to the fourth position to twist the second portion of the suture around itself to form a twisted shape; and releasing the second end and the fourth position, wherein the step of twisting is performed with a number of twists and at a specific tension such that, upon release, the second portion remains twisted.

In a further embodiment, the present invention is a method of forming a suture including a first portion and a second portion with a rounded shape and a third portion, in between the first and second portions, with a flat shape, the method including the steps of: obtaining a suture having a flat shape along its entire length between a first end and second end; holding the first end and holding a first position along the length, the first position designating a transition from the first portion to the third portion; manipulating the first portion to change the shape from the flat shape to the rounded shape; holding the second end and holding a second position along the length, the second position designating a transition from the second portion to the third portion; manipulating the second portion to change the shape from the flat shape to the rounded shape; releasing the first end and the first position, wherein the first portion maintains the rounded shape; and releasing the second end and the second position, wherein the third portion maintains the second shape.

In yet another embodiment, the present invention includes a method of making suture comprising the steps of: forming a bulk length of suture having a flat shape along its length; selectively manipulating portions of the length to alter the flat shape into a rounded shape at the selected portions; and cutting the bulk length into sections, each section including at least one portion having a flat shape and at least one portion having a rounded shape.

In still a further embodiment, the present invention includes a suture having a length and a flat cross-section, comprising: a first portion, defined between a first end of the suture and a first position along the length of the suture, manipulated such that the first portion has a rounded shape; a second portion, defined between the first position and a second position along the length of the suture; and a third portion, defined between the second position and a second end of the suture, manipulated such that the third portion has a rounded shape. Further, the structure of the entire length of the suture, from the first end to the second end, preferably maintains a flat cross-section. The manipulation may be twisting, where the first portion is twisted on itself to form the rounded shape, and the third portion is twisted on itself to form the rounded shape.

BRIEF DESCRIPTION OF THE DRAWINGS

FIGS. 1-7 illustrate exemplary embodiments of the present invention to provide additional clarity as to the methods and techniques that could be undertaken to create a suture having varying cross-sectional shapes along its length.

FIG. 1 illustrates one embodiment of the present invention including a flat suture with a twisted first portion such that the first portion has a different shape from a second portion which was not twisted and maintains the flat shape.

FIG. 2 illustrates another embodiment of the present invention including a flat suture with the twisted first portion as in FIG. 1, including a heat treatment step to reinforce the twisted shape.

FIG. 3 illustrates one embodiment of a device adapted to create a first portion having a different shape or cross-section from the rest of the suture, and further the device can reinforce such formed first portion.

FIGS. 5A-5B illustrate a further embodiment of the present invention including a flat suture whereby the first portion, having a different shape from the flat suture, is formed using a tubular device.

FIG. 6 illustrates another embodiment of the present invention including a flat suture whereby the first portion, having a different shape from the flat suture, is formed by at least one cut.

FIG. 7 illustrates one embodiment of a machine used to form the twisted first portion as in FIG. 1, including a heat treatment step to reinforce the twisted shape as in FIG. 2.

DETAILED DESCRIPTION

Figure 1:
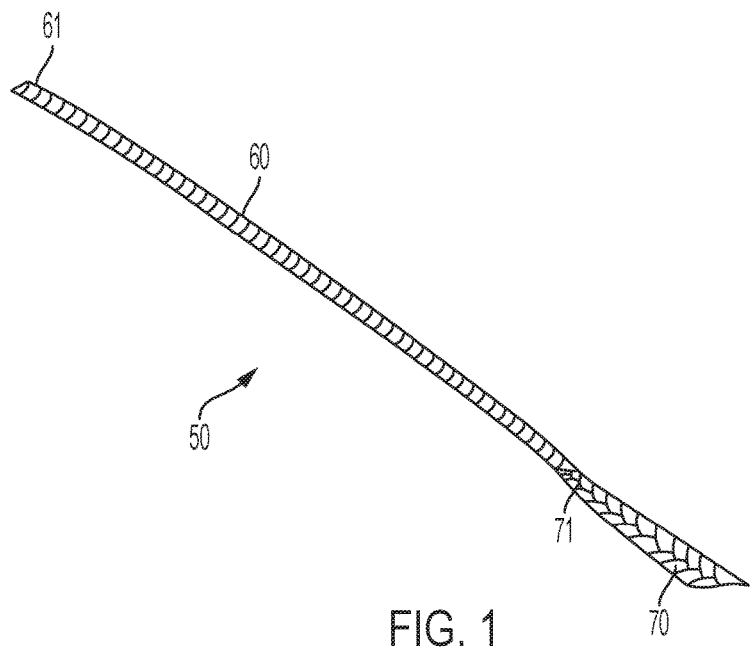

Surgical flat sutures are the next generation of high strength sutures. Such flat sutures, often times referred to as tape or suture tape, can provide a wider footprint on top of tissue which may induce better contact between the tissue and underlying bone, if present, as well as to prevent or reduce damage to the tissue. As to the former benefit, a larger footprint may allow for better tissue fixation and adhesion to underlying bone during a surgical repair. As to the latter benefit, standard, round sutures may impart a holding force on a smaller surface area of the tissue which could lead to tearing or cutting into the tissue by the suture.

As discussed above, flat sutures presently have the significant drawback of being incompatible with standard instrumentation. In order to facilitate the handling of the flat sutures during surgery, and to make such flat sutures compatible with standard instrumentation, the present invention generally concerns different methods and techniques to alter portions of the flat suture to have varying cross-sections and shapes. Preferably, the various embodiments of the present invention form a suture with a varying cross-section along its length. For example, the various embodiments of the present invention can be used on a suture having a flat shape to form a portion with a rounded shape such that such portions may mimic the shape of standard sutures which can thus be used with standard instrumentation designed to handle rounded sutures. "Rounded" is defined as a round, circular, ovular, or other such shape. For example, the rounded or varying cross section formed by the present invention more closely mimics a standard suture shape and thus provides certain characteristics that allow compatibility with a wider range of surgical equipment such as tools to pass suture through tissue, suture weaving tools, etc. In one example, the method disclosed herein can be used to form a suture length having a "round-flat-round" configuration, where the two ends of the suture are rounded and the middle of the suture remains flat.

It is appreciated that the embodiments of the present invention are not limited to forming portions of a flat suture into a different shape or cross-section, and thus it is envisioned that the modified portions do not necessarily need to be rounded but can have a different cross-section or shape. Further, it is envisioned that this invention can be used on other sutures than flat sutures to form portions of such a suture into different shapes from the starting shape of the suture. However, for the sake of clarity, the illustrative embodiments herein will be described as being applied to a flat suture to create portions of different cross-sections and shapes, and in particular rounded shapes and cross-sections thereon.

The methods of the present invention can be utilized on any type, material or size of surgical sutures desired. For example, as to flat sutures used in orthopedic applications, such suture tapes having a width of about 0.9 mm up to about 3.0 mm are commonly used. Such sutures are typically braided or woven from a plurality of fibers. Further, such sutures are normally constructed of ultrahigh molecular weight polyethylene (UHMWPE), either in its entirety or woven in combination with other materials such as polyester, polypropylene, silk, nylon or the like.

As used herein for the sake of simplicity, a "first portion" is defined as a portion of a length of suture that undergoes manipulation via one of the described methods herein. In other word, the first portion is defined as the portion of the suture that is manipulated to having the varying or altered cross-section or shape different from the starting shape or cross-section of the suture.

FIG. 1 illustrates one embodiment of the result of a method of forming a portion of a flat suture 50 into a different shape or cross-section. Specifically, a first portion 60 of the flat suture 50 is formed into a rounded shape, such as a shape that more closely mimics a standard suture, through a manipulation technique. For example, the manipulation is a twisting technique. As such, the flat suture is securely held at a first end 61 and at a second position 71 at a desired location in between the first and a second end. Such desired length determines the length of the first portion 60 which will have the rounded shape. With the two locations held securely, one location is rotated around a longitudinal axis of the suture relative to the other to twist the first portion of the suture around itself, forming a twisted shape. For example, the flat suture, upon twisting, will form a generally helical shape such that it winds on itself into a rounded shape.

It should be noted that, while the cross-section or shape of the first portion 60 of the suture forms a rounded shape, the cross-section of the suture material itself remains generally flat. The flat suture maintains its shape but simply forms a helical pattern to generate the rounded shape. In other words, the flat shape is not altered but simply twists onto itself such that the resulting first portion forms a rounded shape or cross-section while the suture material itself, within the first portion, maintains its flat, but twisted, cross-section.

Continuing with this embodiment of FIG. 1, during the twisting step, the first portion 60 undergoes multiple tensions, including at least the tension of the twisting itself, as well as longitudinal tension to maintain tautness of the first portion 60. These forces applied to the first portion may maintain the first portion in this rounded shape even after the first end 61 and second position 71 are released. As such, following the twisting step, the first end and second position are released and the first portion remains in the twisted configuration while the rest of the suture (designated generally as portion 70) remains in the initial flat shape, as illustrated in FIG. 1.

In another embodiment, the manipulated configuration of the first portion may be reinforced by a stiffening agent. The stiffening agent can be applied to the first portion at any time to reinforce the manipulated suture portion such that it maintains its manipulated shape. In other words, the stiffening agent may not necessarily stiffen or harden the first portion, though the stiffening agent should reinforce the manipulated shape such that it will not easily come undone. For example, as to the twisting technique described above, the stiffening agent can be applied either before or after the first end and the second position are released, though it is preferable to apply the stiffening agent prior to release in order to maintain the twisting and tensioning forces on the first portion such that the first portion is reinforced when in such a tightly wound configuration. This way, the first portion may still be bent, twisted, tied, and the like, as a normal suture, but the new shape of the first portion would be secured such that the shape could not easily, if at all, revert back to a flat or rectangular shape.

Figure 2:
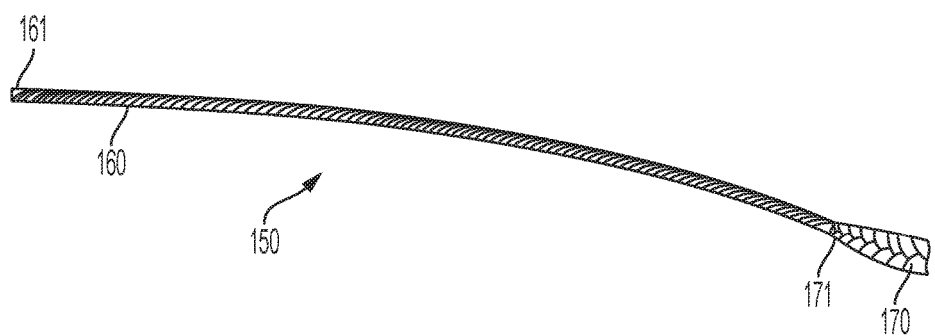

The stiffening agent may be any mechanical, chemical or other such force, energy or substance sufficient to help maintain the first portion in the twisted configuration. For example, as in FIG. 2, the stiffening agent is in the form of energy, specifically heat, applied to the first portion 160 of flat suture 150. Once the first portion is formed through twisting, as discussed above relative to FIG. 1, energy is applied to the suture to maintain the rounded shape in the first portion while the rest of the suture (designated generally as portion 170) remains in the initial flat shape, as illustrated in FIG. 2. Heat, for example, can be applied in a variety of ways, such as for example, the use of a heat gun or the like, or through the addition of a mechanical force such as one or more heated plates, heated plates with rounded cavities to provide better circular definition (similar to the press illustrated in FIGS. 3 and 4A-C), heated rollers, hot air, or the like. Further alternatives could include techniques including ultrasonic or laser welding, or the like. The energy applied to the first portion 160 may heat the fibers near their glass transition temperature(s), such that upon cooling, they may at least partially adhere to one another and/or maintain their newly intertwined or inter-twisted morphology to reinforce the twisted configuration.

In a further embodiment, similar to that described above as to FIG. 2, the heat can instead be applied at intermittent locations along the first portion 160, including the first end 161 and at the second position 171. In this method, the applied heat forms "tack welds" at desired points along the first portion. Such tack welds may be sufficient to reinforce the twisted configuration while also requiring less time and energy during manufacture than heating the entire first portion, as described above relative to FIG. 2.

In still another embodiment, once the manipulation technique forms a first portion, such as by the twisting technique discussed above, a stiffening agent such as a silicone, glue or the like is applied to at least part of the first portion to maintain the rounded shape. As with the heat in the above embodiments, the silicone or glue assists in maintaining the twist by adhering the fibers to one another and/or maintain their newly intertwined or inter-twisted morphology.

In yet a further embodiment, the manipulated shape of a first portion may be reinforced using an additional suture which is sewn into at least part of the first portion. The additional suture may secure the first portion in the manipulated (for example, a twisted) configuration.

In addition to the above embodiments including the manipulating, such as twisting, of the first portion of the flat suture, other methods may be used to form a varying cross-section or shape on the suture that may include other types of manipulation other than twisting. While the below embodiments are described by manipulating the first portion through folding, compressing, crimping, or cutting, they may be used in conjunction with twisting (as described above) or in place of twisting.

Figure 3:
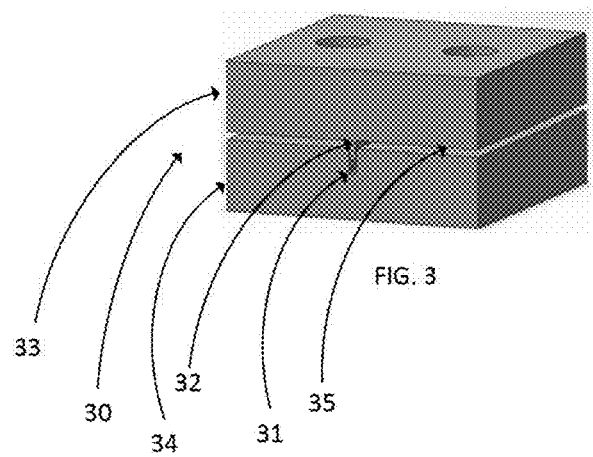

In one embodiment, through the use of a mechanical force in addition to heat, illustrated as heated plates 33, 34 of shaping device 30, as illustrated in FIG. 3, a first portion of the suture is manipulated by placing a portion of the suture over the cavity 31 and in the interplate space 35. As the top plate 33 is brought into contact with the bottom plate 34, the ridge 32 of the top plate contacts the suture and folds it in half and forces it into the cavity 31. As a result, the first portion is formed in the suture by changing the shape or cross-section of the first portion of the suture from a flat configuration to a folded configuration.

With the first portion of the suture formed by folding of the suture, heat may then be applied to reinforce and secure the fold. The suture may then be removed from the cavity and the first portion remains in its folded configuration.

Figure 4A:
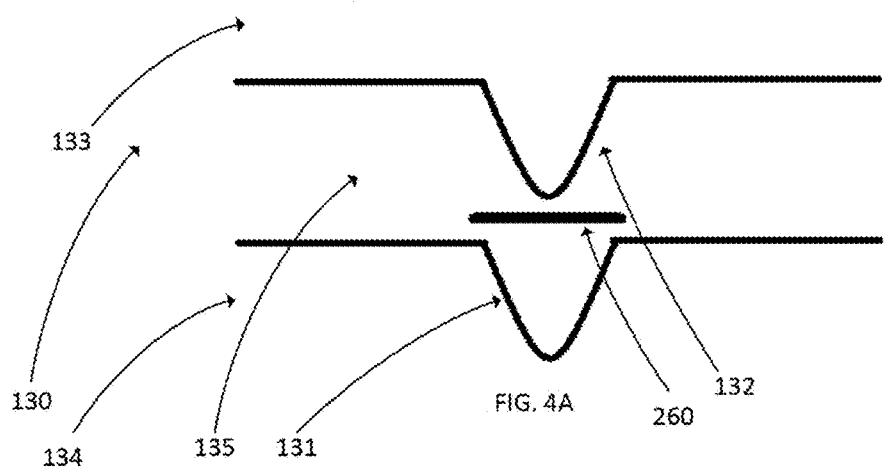
FIGS. 4A-4C illustrate a schematic of another embodiment of a device adapted to create a first portion having a different shape or cross-section from the rest of the suture, and further the device can reinforce such formed first portion.
Figure 4B:
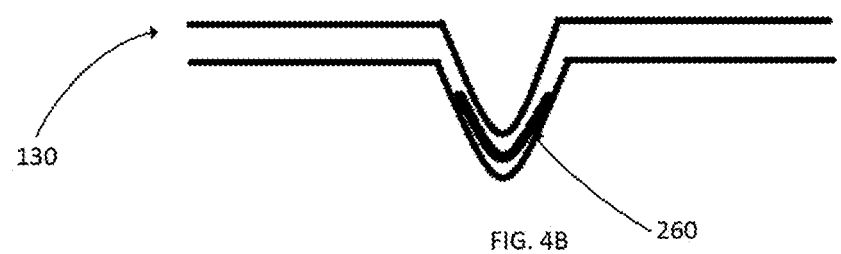
Figure 4C:
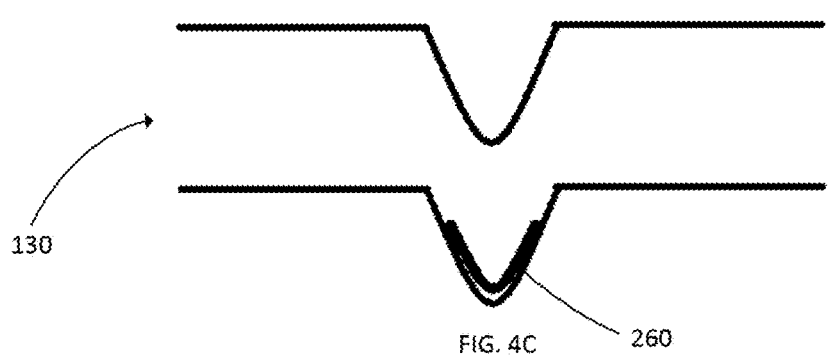

FIGS. 4A-4C are a schematic of the method of forming a first portion 260 of a suture into a different shape or cross-section using opposing heating plates 133, 134 of shaping device 130 as illustrated for example in FIG. 3. As illustrated in FIG. 4B, for example, the suture is pressed by ridge 132 into cavity 131 and in the interplate space 135, thereby forming the first portion 260 as a U-shape. While held in this position, the heated plates may reinforce and secure this fold. Of course, while the cavity and ridge are shown as having a generally triangular cross-section, they may have a rectangular cross-section or any other shape suitable to fold or compress the first portion 260 into a different shape.

In another embodiment, illustrated in FIGS. 5A-5B, a tubular device 40, such as a plastic tube, may be positioned over a first portion 360 of the suture tape. The plastic tube may be thermoreactive such that, upon application of heat to the plastic tube so positioned on the suture (FIG. 5A), the plastic tube shrinks around the suture (FIG. 5B). As the tube shrinks, the portion of the suture within the tube is manipulated such that it compresses, crushes, and/or folds to form a shape or cross-section different from that of the rest of the suture. As such, the first portion of the suture, having a shape different from the rest of the suture, constitutes the length of suture within the plastic tube. Upon cooling, the tube maintains its compressed shape, and thus, maintains the shape of the first portion of the suture.

Alternatively, rather than using a thermoreactive plastic tube as above, silicone tubing may instead be used. The silicone tubing may be stretched to fit around a portion of the flat suture. Once in position around the suture, the silicone tube is allowed to return to its original shape, thereby compressing a portion of the suture within the tube. As a result, as above, the first portion is manipulated as the tube compresses, crushes, and/or folds to form a shape or cross-section different from that of the rest of the suture.

In still a further embodiment, the first portion of the suture is manipulated by mechanical forces without the use of heat. For example, a portion of the suture may be rolled, folded, twisted, or the like and subsequently subjected to rolling, crushing, or the like. The secondary mechanical forces applied to the suture may reinforce the reconfiguration of the first portion and may hold the first portion in its new configuration.

Similarly, rather than subsequent mechanical forces, the manipulated first portion may instead be exposed to one of the other stiffening agents discussed above, such as adhesive, sewing with another suture, or the like.

FIG. 6 illustrates yet another embodiment of the present invention. Rather than the mechanical steps of manipulation discussed above, such as twisting, folding or compressing, the first portion 460 of the suture may instead be manipulated using at least one cut 462 to alter the shape of a portion of the suture, creating the first portion having a different shape or cross-section. As illustrated, for example, two cuts extending from one end 461 of the suture may be formed such that at first end 461, about two thirds of the width of the suture is removed, creating the first portion. As illustrated, the cuts may be tapered such that the resulting first portion gradually widens to meet the width of the original suture, though the cuts may be parallel to the longitudinal axis of the suture, include at least one step, have a curved or irregular path, or the like. The cuts may be formed using known suture cutting instruments such as scissors, a surgical knife, a hot knife, or the like. Unlike the other embodiments above, this technique utilizing cuts on the shape of the suture would alter the original "flat" cross-section of the suture to have at least a shorter width than the original cross-section. As with the other embodiments, this cutting step may be performed during manufacture of the suture, on an off-the-shelf suture, immediately prior to the surgical procedure, or the like.

In yet other embodiments, the braid of the suture itself may be altered to manipulate the shape or cross-section of a portion of the suture. For example, fraying one end of the suture, thereby removing fibers from the braid, may alter the shape of the suture to create a change in shape that is, for example, closer to a standard suture. For example, fraying the flat suture to remove portions of the suture could narrow the suture, creating the first portion of a different shape or cross-section. Such a method reduces the overall number of fibers in the formed first portion of the braid, resulting in a smaller or altered shape from the original flat shape. In one embodiment, such fraying may be performed using a wire wheel, wire brush, or the like. In another alternative, following fraying, any of the above techniques (such as twisting, application of heat, etc.) may be used to further change and/or reinforce the change in shape.

In another embodiment, after the suture end is frayed, the fibers of the braid may be re-braided in a different configuration to form a different shape or cross-section, and thus, form the first portion of the suture. Of course, contrary to the other embodiments above, these fraying and/or re-braiding techniques would destroy the "flat" cross-section of the suture itself, and result in an altogether different cross-section of the suture.

The above technique may be used to form sutures of varying cross-section or shape at multiple locations along their length. For example, a rounded shape may be formed along one portion of the suture, while an oval shape can be formed along another portion. Further, a folded shape may be formed at still another portion. Similarly, a combination of any of the above methods may be used on a single length of suture. For example, the first end may be subject to the heat and twisting technique, while the second end may be subject to the shrink-fit plastic tubing. Any such combinations are envisioned.

Any of the above methods can be performed during manufacture of the suture itself or performed subsequent to preparation of suture, such as an after-market method on an off-the-shelf suture. For example, in one embodiment, the above methods may be performed immediately following the braiding of the suture itself, such that a suture having varying cross-section is formed in a single manufacturing process. In another embodiment, any of the above methods can be performed on an already-formed length of suture, where a standard flat suture is taken "off the shelf" and one of the methods is then performed on the suture to form the varying cross-sectional shape. In yet another embodiment, the present invention may be performed on a bulk length of a suture wherein portions of a bulk length (either immediately after braiding or as an independent manufacturing process) are subject to any of the above methods to form the varying cross-section or shapes. Subsequent to forming the varying cross-sections, the bulk length is then cut at desired lengths. Preferably, the cuts of the bulk length would occur such that the treated portions are on the ends, and the flat portions are in the middle, of each cut suture.

Figure 7:
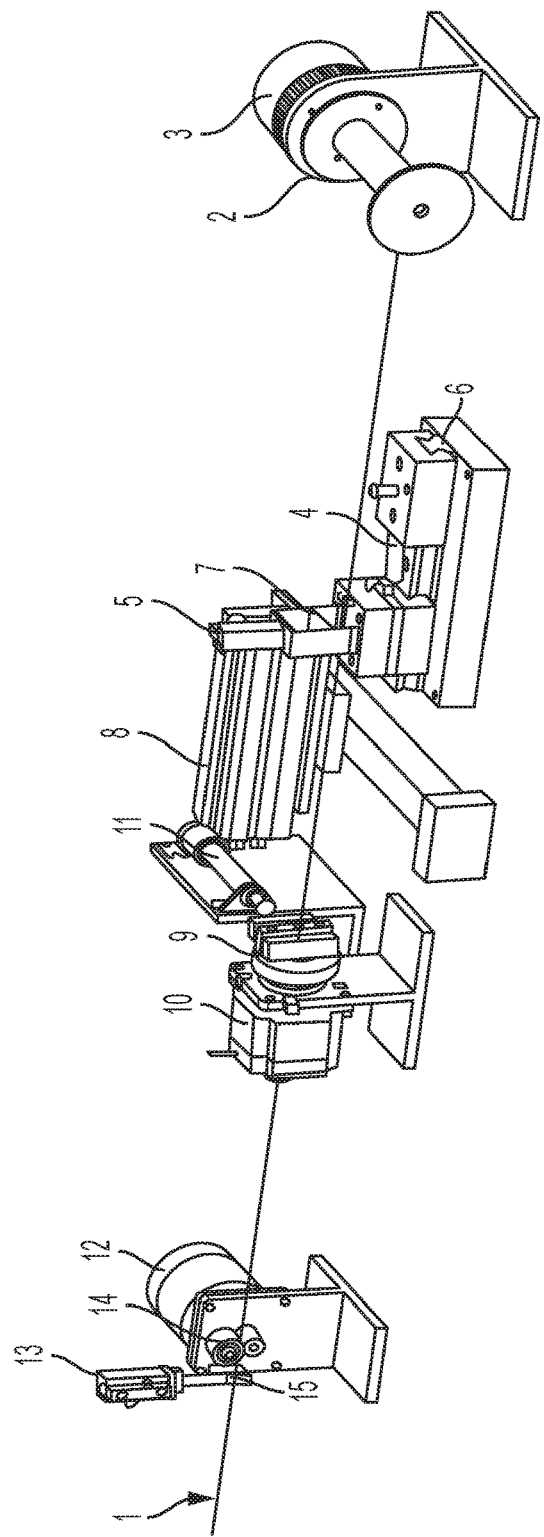

One embodiment of a machine suitable for use in performing a manipulation of suture is illustrated in FIG. 7. In this exemplary machine, to summarize, a bulk length of suture can be manipulated to include at least one portion having a varying cross-section or length. Specifically, by holding the suture at a first location 7 and a second location 9, and rotating the second location 9 (the rotary clamp), a twist is formed in the suture between the locations 7, 9 (similar to forming the first portion). For example, the first location 7 may be a clamp that secures the suture. Further, the first location 7 may be longitudinally slideable, via spring 4, such that, upon clamping at locations 7 and 9, tension can be maintained on the suture during twisting. Such tensioning can, for example, minimize the suture from kinking during twisting. For example, the spring may exert a force, as a constant spring force, of any amount desired, though preferably the force is about 2 to about 5 pounds, more preferably about 4.1 pounds. Similarly, the second location 9 includes a clamp, which is biased in the closed position but can be opened via pneumatic piston 11 to allow the suture to move longitudinally through the machinery. Clamp 9 is further rotatable to perform the twisting step, and can be preprogrammed to a desired number of rotations or twists. The amount of twists imparted on the first portion can be any amount desired. In one example, the number of twists could be between about 5 twists per inch and about 15 twists per inch, and more specifically about 5 to about 10 twists per inch. In a specific example, the distance between the first location 7 and second location 9 can be about 8 inches. For a flat suture with a width of about 1.2 mm, the machine may rotate the first location relative to the second location about 65 times, while for an about 2.0 mm width, the number of rotations may be about 80. The actual number of rotations can be adjusted based on various factors. For instance, a greater number of rotations (or twists) results in a stronger twisted portion, but the portion is also stiffer and more difficult to manipulate during surgery. The converse is true for fewer rotations.

Continuing with this embodiment, once the twist is formed, the heating element 8 (heating plate, or the like) is applied to at least part of the twisted portion to reinforce and maintain the twist. The heating plate includes a channel within which the twisted suture may be positioned, though other surface features are envisioned. A second heating plate may be positioned opposite heating element 8 to clamp around the circumference of the suture, and may include a similar channel, a rib to position within the channel, a flat surface, or the like. The heating element 8 may operate at a temperature of between, for example, about 260 and about 400 degrees Fahrenheit. The desired temperature and time exposing the suture to the heating plates is determined based on the size of suture being manufactured. For example, for a flat suture having a width of 1.2 mm, the parameters might include a temperature of about 320 to about 390 degrees Fahrenheit for a period of about 2 to about 10 seconds. In one particular working example, the parameters for this width of suture may be about 360 to about 380 degrees Fahrenheit for about 3.5 seconds. In another working example, the parameters for this width of suture may be about 330 to about 350 degrees Fahrenheit for about 8 seconds. In another example, for a flat suture having a width of 2.0 mm, the parameters might include a temperature of about 320 to about 400 degrees Fahrenheit for a period of about 5 to about 10 seconds. In one particular working example, the parameters for this width of suture may be about 370 to about 390 degrees Fahrenheit for about 8 seconds. In another working example, the parameters for this width of suture may be about 330 to about 350 degrees Fahrenheit for about 6 seconds.

Upon release of the first and second locations 7, 9, the twisted portion moves along the manufacturing process to blade 15 (knife, cutting wheel, or the like). Preferably in this embodiment, the blade 15 is positioned at about the midpoint between the first and second locations 7, 9 (i.e., in the middle of the twisted portion). Thus, in this embodiment, upon making this cut (via the pneumatic actuation 13 to move blade 15), a first portion is formed on two adjacent suture lengths—e.g., from a first end of each suture length (effectively formed at the point of cutting) to a second position along the length of each suture (effectively defined at locations 7 and 9). Continuing with the earlier example of an 8 inch length between first and second locations 7, 9, this would result in a first portion on each formed suture of about 4 inches, depending on the actual coverage of the heating plates between locations 7, 9. The process is then repeated on a second portion of the bulk length of suture. Of course, the bulk length of suture can be applied to this machine directly from the suture manufacturing machinery (e.g., the braiding machinery), or alternatively the bulk length of suture can be "off-the-shelf."

Further, in a preferred embodiment, a suture having a first portion, a second portion and a third portion may be formed by the above techniques. Specifically, as in FIGS. 1 and 2, the first portion, defined between a first end of the suture and a first position along the length of the suture, is manipulated, such as by being twisted on itself, such that the first portion has a rounded shape. This first portion may be heat treated, or subject to another stiffening agent, as discussed above. The second portion, defined between the first position and a second position along the length of the suture, constitutes a middle portion of the suture that remains unchanged (i.e., maintains its flat or rectangular shape). The third portion (not shown), defined between the second position and a second end of the suture, is manipulated, such as by being twisted on itself, such that the third portion has a rounded shape. Similar to the first portion, a stiffening agent may be applied to maintain the third portion in its rounded shape. While the actual structure of the suture, along its entire length from first end to second end, remains the same (i.e., a flat cross-section), the overall shape and cross-section of the suture is altered along its first and third portions. In other words, with specific reference to the twisting technique for example, the flat cross-section remains along its length, though along the first and third portions the flat cross-section is twisted or otherwise compressed or folded such that the first and third portions look as if their shape and cross-section is that of a circle or oval.

As such, having rounded sections allows these sutures to be manipulated with standard instrumentation, used with standard suture anchors, form tight knots with less likelihood of such knots loosening, be adapted for splicing to make more complex constructs and allow for varying cross sections on different areas of tissue.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of forming a suture having various cross-sectional shapes, the method comprising the steps of:
   braiding the suture such that the suture has a first cross-sectional shape along a length;
   holding a first end of the suture and holding the suture at a second position at a location in between the first end and a second end such that a first portion of the suture is defined between the first end and the second position;

manipulating the first end relative to the second position to alter the first portion of the suture into an altered cross-sectional shape different from the first cross-sectional shape; and releasing the first end and the second position, wherein the step of manipulating is performed such that, upon release, the first portion maintains its manipulated shape.

2. The method of claim 1, wherein the manipulating step comprises twisting the first portion around an axis defined along the length of the suture.

3. The method of claim 2, wherein the first cross-sectional shape is flat and the altered cross-sectional shape is rounded.

4. The method of claim 3, wherein the twisting of the first portion winds the flat cross-sectional shape into a helical pattern, the helical pattern forming the rounded cross-sectional shape.

5. The method of claim 1, further comprising the steps of:

holding a second end of the suture and holding the suture at a fourth position at a location in between the second position and a second end, and spaced from the second position, such that a second portion of the suture is defined between the second end and the fourth position;

manipulating the second end relative to the fourth position to alter the second portion of the suture into an altered cross-sectional shape different from the first cross-sectional shape; and releasing the second end and the fourth position, wherein the step of manipulating is performed such that, upon release, the second portion maintains its manipulated shape.

6. The method of claim 5, wherein the manipulating step comprises twisting the second portion around an axis defined along the length of the suture.

7. The method of claim 6, wherein the first cross-sectional shape is flat and the altered cross-sectional shape is rounded.

8. The method of claim 7, wherein the twisting of the second portion winds the flat cross-sectional shape into a helical pattern, the helical pattern forming the rounded cross-sectional shape.

9. The method of claim 1, further comprising the step of, after the manipulating step, applying a stiffening agent to the first portion to reinforce the first portion in its manipulated shape.

10. The method of claim 9, wherein the stiffening agent is heat applied to the first portion.

11. A method of forming a suture including a first portion and a second portion with a rounded shape and a third portion, in between the first and second portions, with a flat shape, the method including the steps of:

obtaining a suture having a flat shape along its entire length between a first end and second end;

holding the first end and holding a first position along the length, the first position designating a transition from the first portion to the third portion;

manipulating the first portion to change the shape of the first portion from the flat shape to the rounded shape;

holding the second end and holding a second position along the length, the second position designating a transition from the second portion to the third portion;

manipulating the second portion to change the shape from the flat shape to the rounded shape;

releasing the first end and the first position, wherein the first portion maintains the rounded shape; and releasing the second end and the second position, wherein the second portion maintains the rounded shape.

12. The method of claim 11, wherein the manipulating steps comprise twisting the first portion and the second portion each around its axis defined along the length of each portion, the twisting of the first portion and the second portion winds the flat shape into a helical pattern, the helical pattern forming the rounded shape.

13. The method of claim 11, further comprising the step of, after the manipulating steps, applying a stiffening agent to the first portion and the second portion to reinforce the first portion and second portion in the rounded shape.

14. The method of claim 13, wherein the stiffening agent is heat applied to the first portion and the second portion.

15. A method of making suture comprising the steps of:

forming a bulk length of suture having a flat shape along its length;

selectively manipulating portions of the length to alter the flat shape into a rounded shape at the selected portions; and cutting the bulk length into sections, each section including at least one portion having a flat shape and at least one portion having a rounded shape.

16. The method of claim 15, further comprising the step of, prior to the cutting step, applying a stiffening agent to the selected portions to reinforce the selected portions in the rounded shape.

17. The method of claim 16, wherein the stiffening agent is heat applied to each selected portion.

18. The method of claim 15, wherein the cutting step includes cutting the bulk length at a location on each of the selected portions, wherein each section includes a portion with a rounded shape at each end and a portion with a flat shape in between the portions with the rounded shape.

19. The method of claim 15, wherein the manipulating step comprises twisting the selected portions around an axis defined along the length of each selected portion.

20. The method of claim 19 wherein the twisting of each selected portion winds the flat shape into a helical pattern, the helical pattern forming the rounded shape.

* * * * *